(12) United States Patent
Seo

(10) Patent No.: US 10,881,941 B2
(45) Date of Patent: Jan. 5, 2021

(54) HYBRID GOLF GUIDE SYSTEM

(71) Applicant: Jong Bok Seo, Namyangju-si (KR)

(72) Inventor: Jong Bok Seo, Namyangju-si (KR)

( * ) Notice: Subject to any disclaimer, the term of this patent is extended or adjusted under 35 U.S.C. 154(b) by 66 days.

(21) Appl. No.: 16/346,103

(22) PCT Filed: Oct. 31, 2017

(86) PCT No.: PCT/KR2017/012165
§ 371 (c)(1),
(2) Date: Apr. 29, 2019

(87) PCT Pub. No.: WO2018/084533
PCT Pub. Date: May 11, 2018

(65) Prior Publication Data
US 2019/0255418 A1    Aug. 22, 2019

(30) Foreign Application Priority Data

Nov. 4, 2016 (KR) .................. 10-2016-0146792

(51) Int. Cl.
*A63B 71/06* (2006.01)
*A63B 69/36* (2006.01)
(Continued)

(52) U.S. Cl.
CPC ...... *A63B 71/0622* (2013.01); *A63B 21/4021* (2015.10); *A63B 24/0003* (2013.01); *A63B 24/0087* (2013.01); *A63B 69/36* (2013.01); *G06Q 10/063112* (2013.01); *G06Q 10/063114* (2013.01); *G06Q 10/063116* (2013.01); *G06Q 50/10* (2013.01); *A63B 2071/0625* (2013.01); *A63B 2071/0691* (2013.01); *A63B 2071/0694* (2013.01); *A63B 2102/32* (2015.10); *A63B 2220/17* (2013.01); *A63B 2220/20* (2013.01); *A63B 2220/70* (2013.01);
(Continued)

(58) Field of Classification Search
CPC ............ A63B 69/3605; A63B 71/0622; A63B 71/0669
See application file for complete search history.

(56) References Cited

U.S. PATENT DOCUMENTS

2008/0058125 A1* 3/2008 Nguyen ................. A63B 57/00
473/407
2015/0105172 A1* 4/2015 Thurman ........... A63B 71/0669
473/199
2016/0354671 A1* 12/2016 Nuesmeyer ....... H04W 52/0254

FOREIGN PATENT DOCUMENTS

KR         10-1081121 B1    11/2011
KR     10-2012-0076510 A     7/2012
(Continued)

OTHER PUBLICATIONS

International Search Report for PCT/KR2017/012165 dated Mar. 13, 2017 from Korean Intellectual Property Office.

*Primary Examiner* — David L Lewis
*Assistant Examiner* — Robert E Mosser
(74) *Attorney, Agent, or Firm* — Revolution IP, PLLC

(57) ABSTRACT

A golf guide system includes a terminal to be carried by a user who is playing golf, and a location information transmitter provided in the terminal and a hole and transmitting location information of the hole to the terminal, generates a distance by measuring a distance between the terminal and the location information transmitter, and guides a distance and a recommendable club based on analysis of environment and geography between the terminal and the hole.

6 Claims, 11 Drawing Sheets

(51) Int. Cl.
*A63B 24/00* (2006.01)
*G06Q 50/10* (2012.01)
*G06Q 10/06* (2012.01)
*A63B 21/00* (2006.01)
*A63B 102/32* (2015.01)

(52) U.S. Cl.
CPC ... *A63B 2220/803* (2013.01); *A63B 2220/836* (2013.01); *A63B 2225/50* (2013.01); *A63B 2225/52* (2013.01)

(56) References Cited

FOREIGN PATENT DOCUMENTS

| KR | 10-2015-0062998 A | 6/2015 |
| KR | 10-2016-0102136 A | 8/2016 |
| KR | 10-1654080 B1 | 9/2016 |

\* cited by examiner

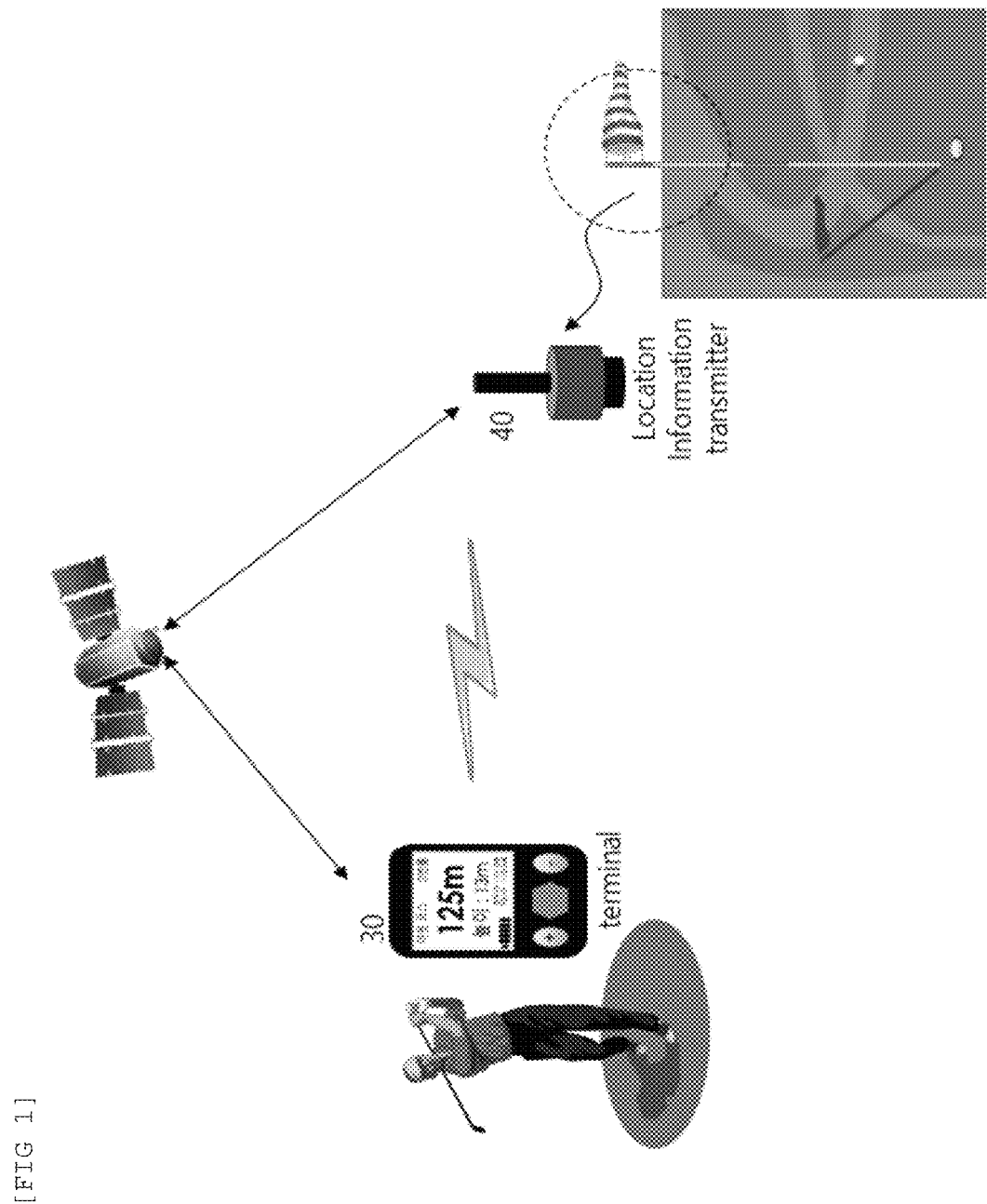
[FIG 1]

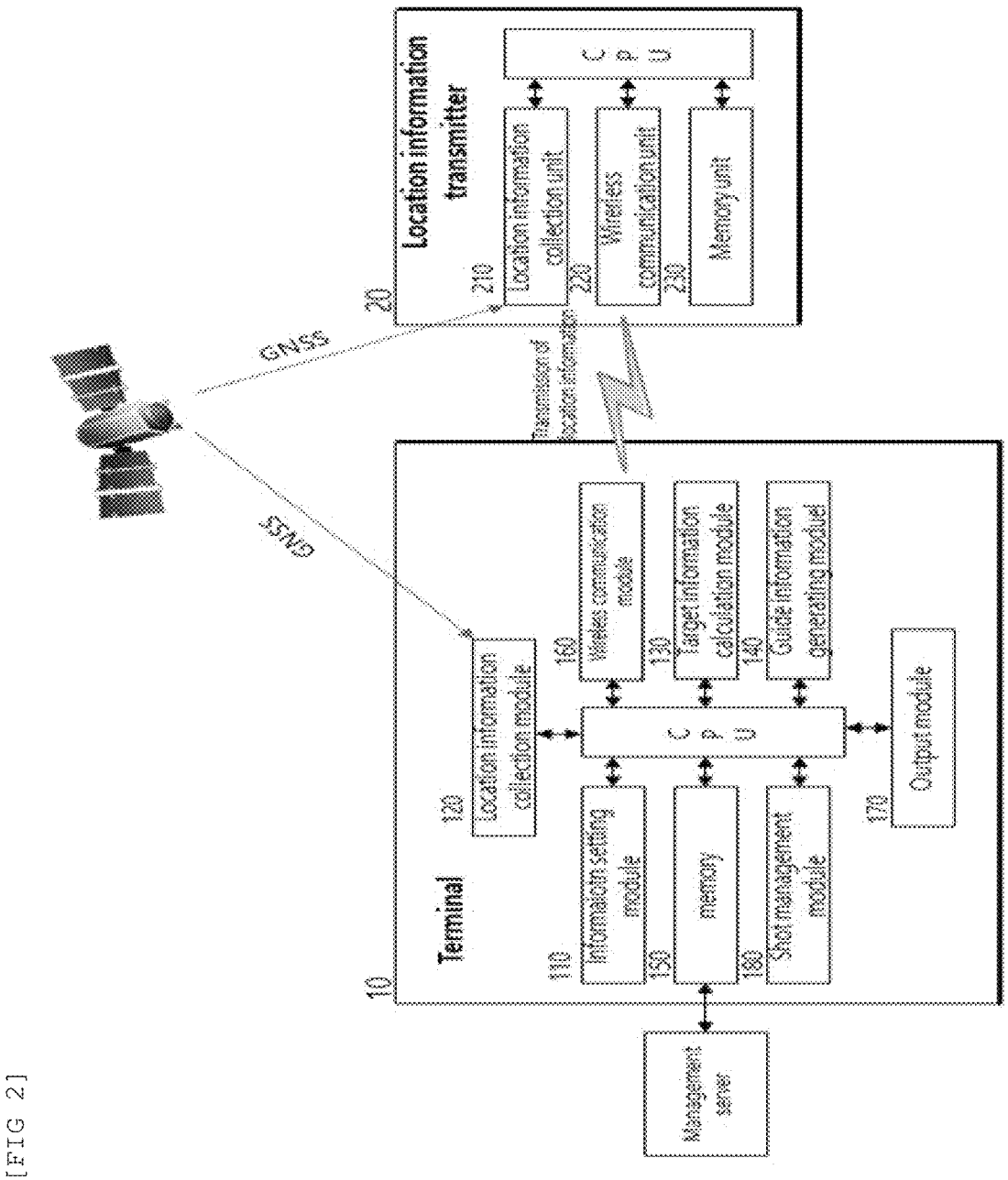
[FIG 2]

[FIG 3]
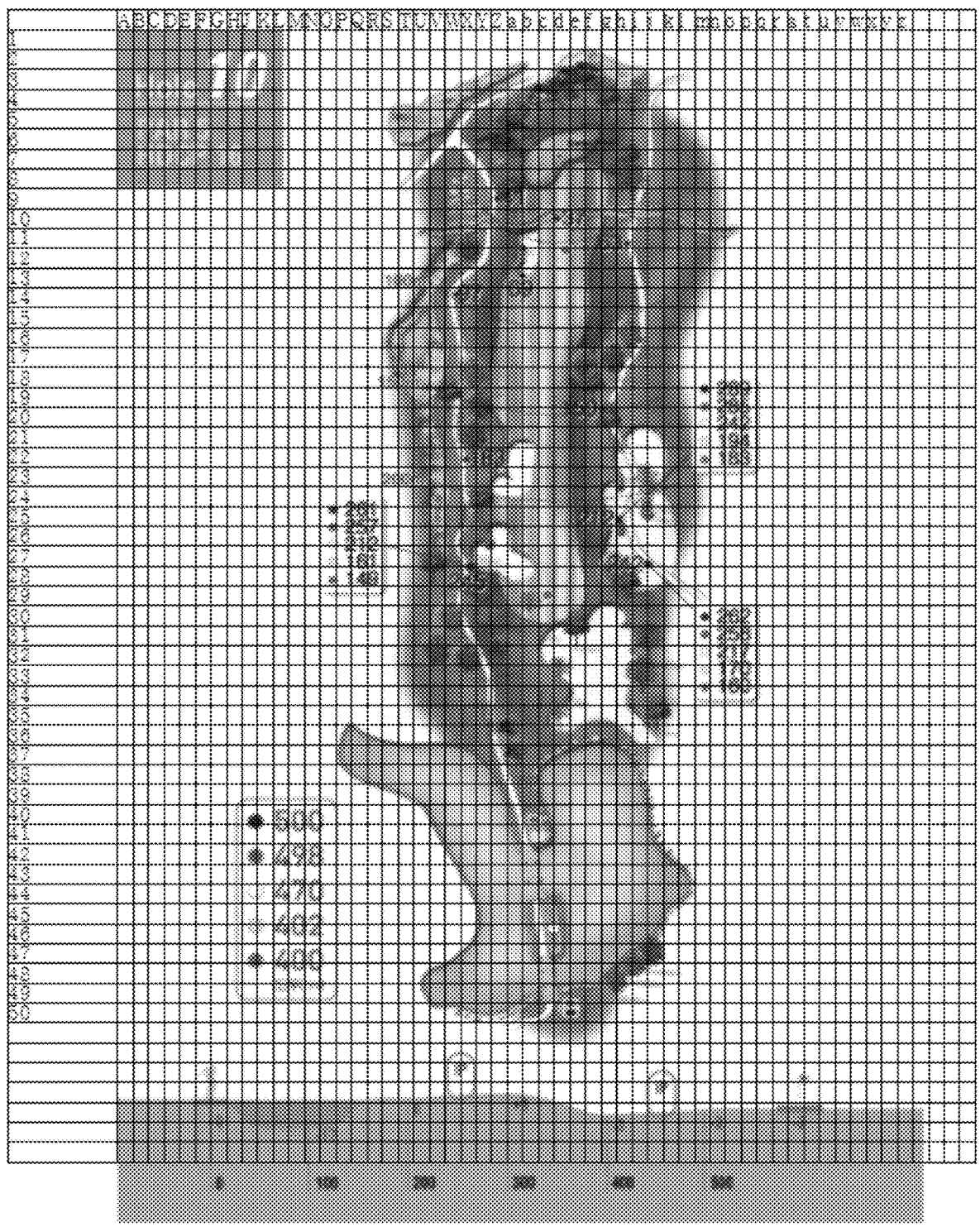

[FIG 4]
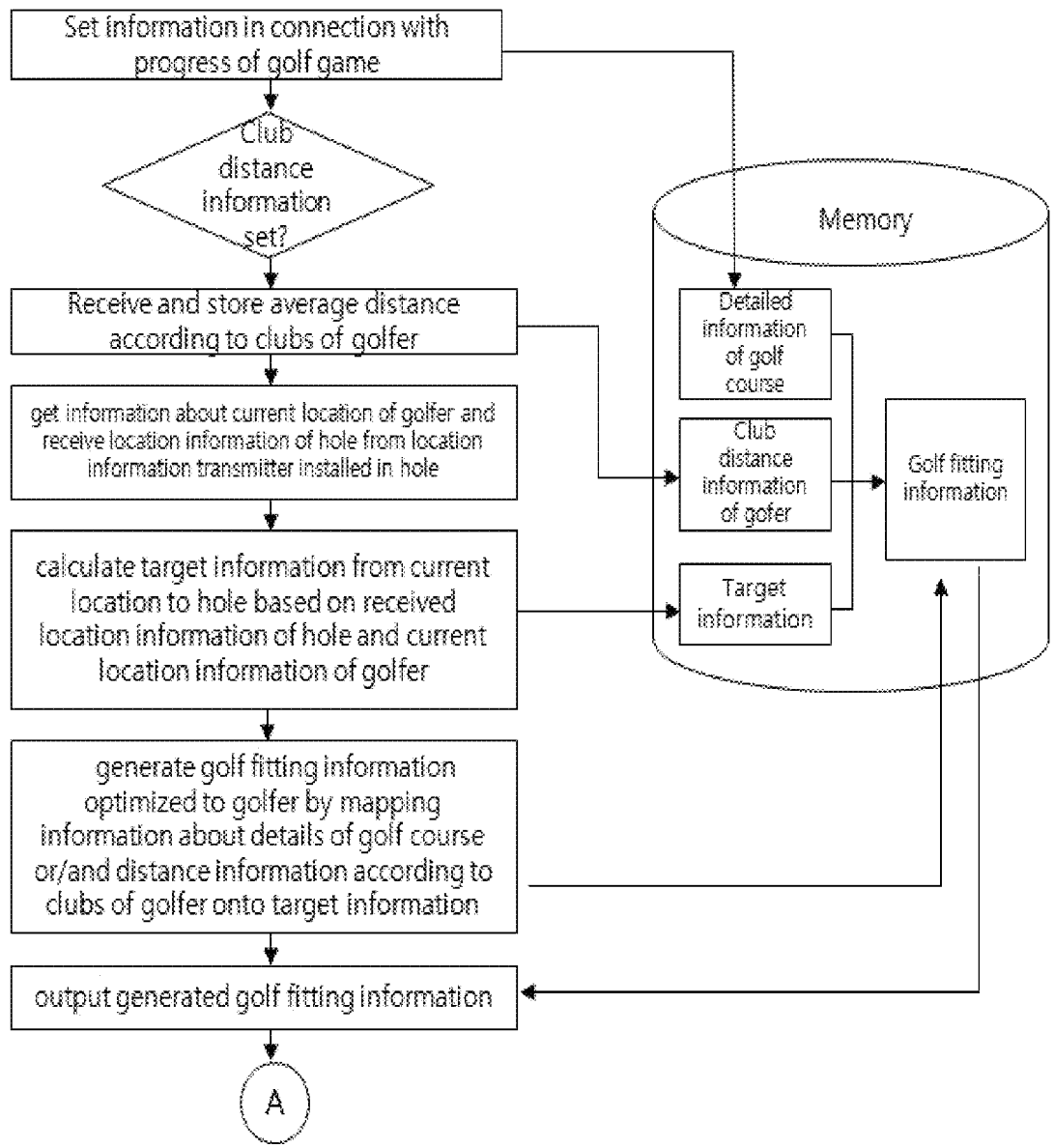

[FIG 5]
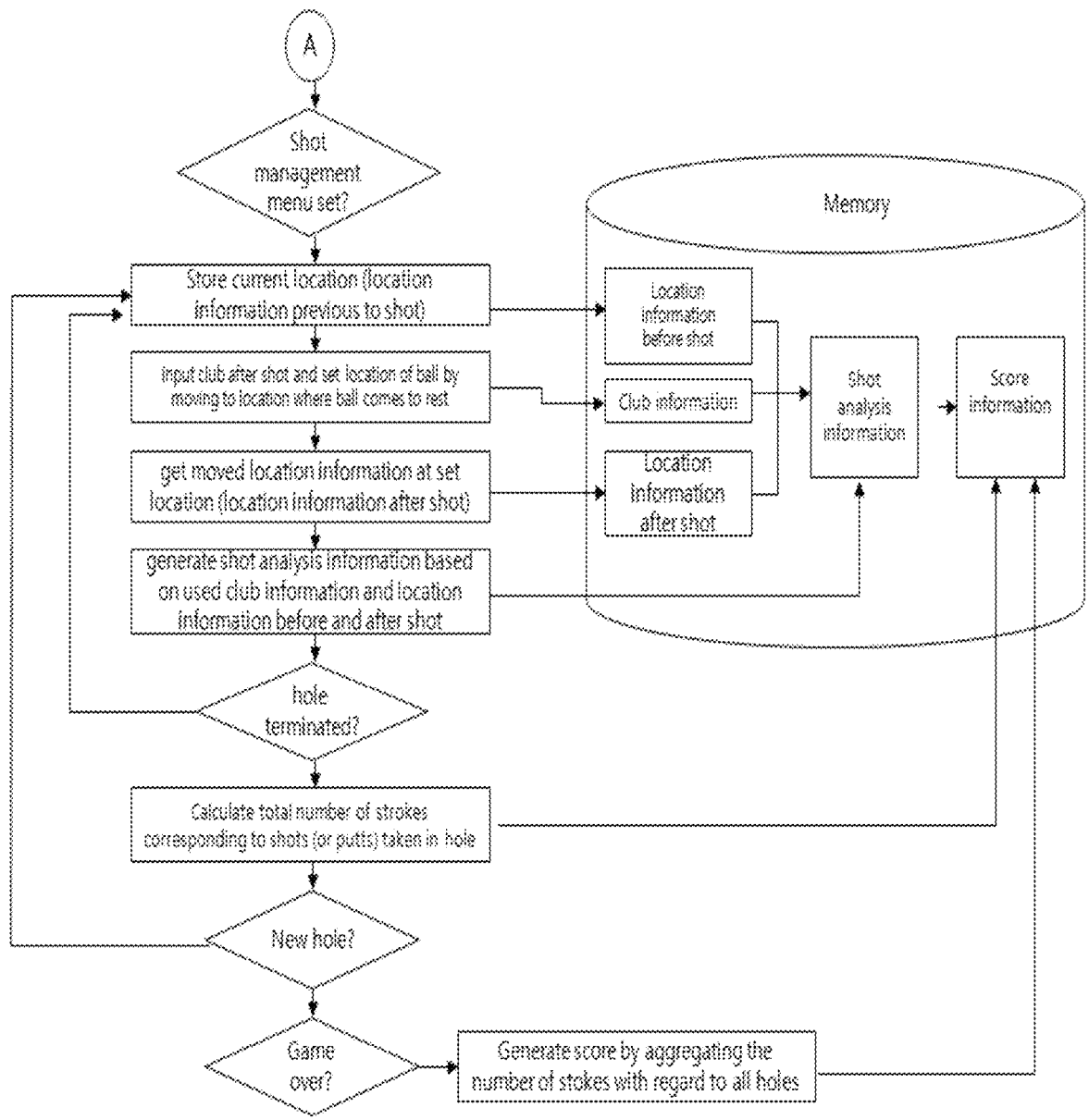

[FIG 6]
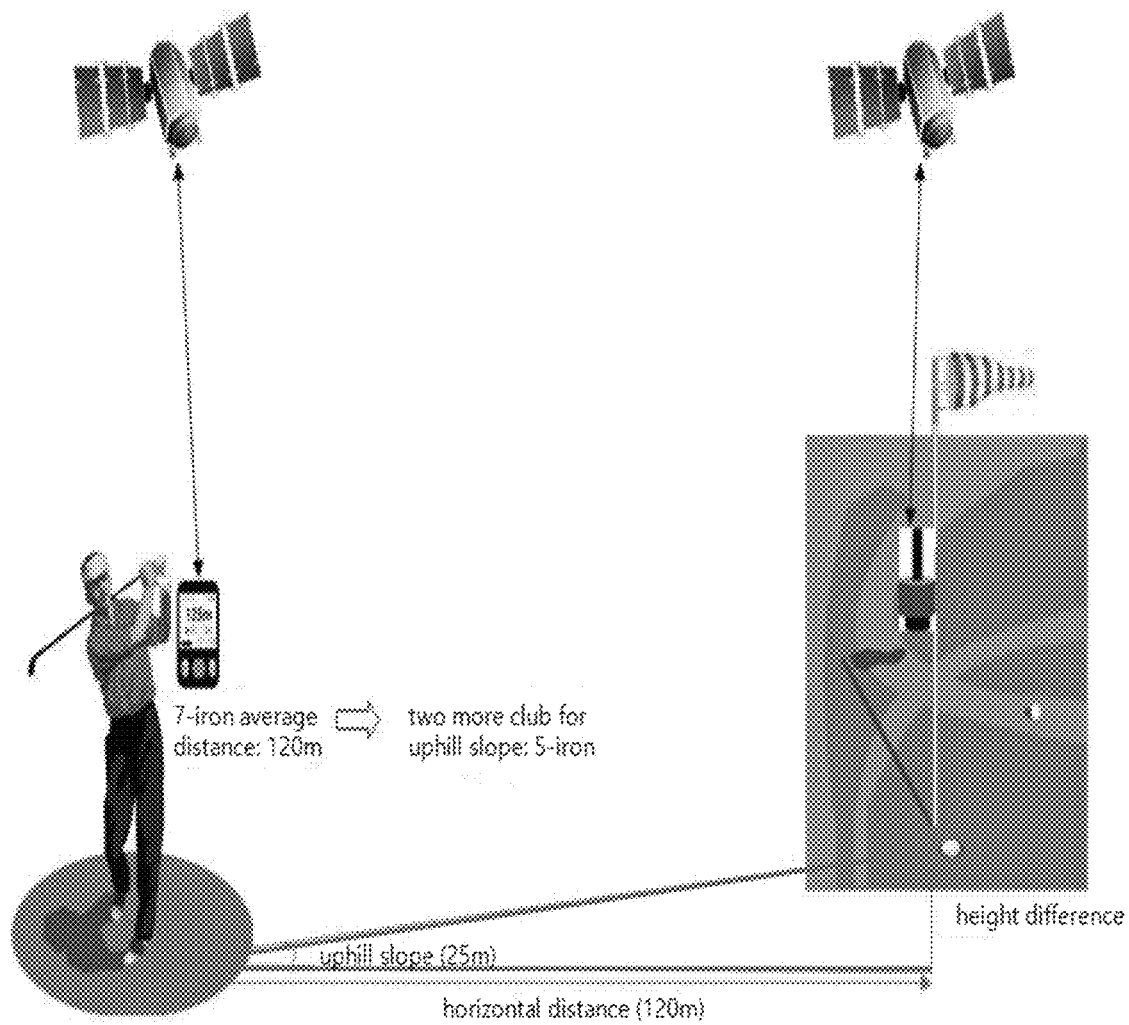

[FIG 7]
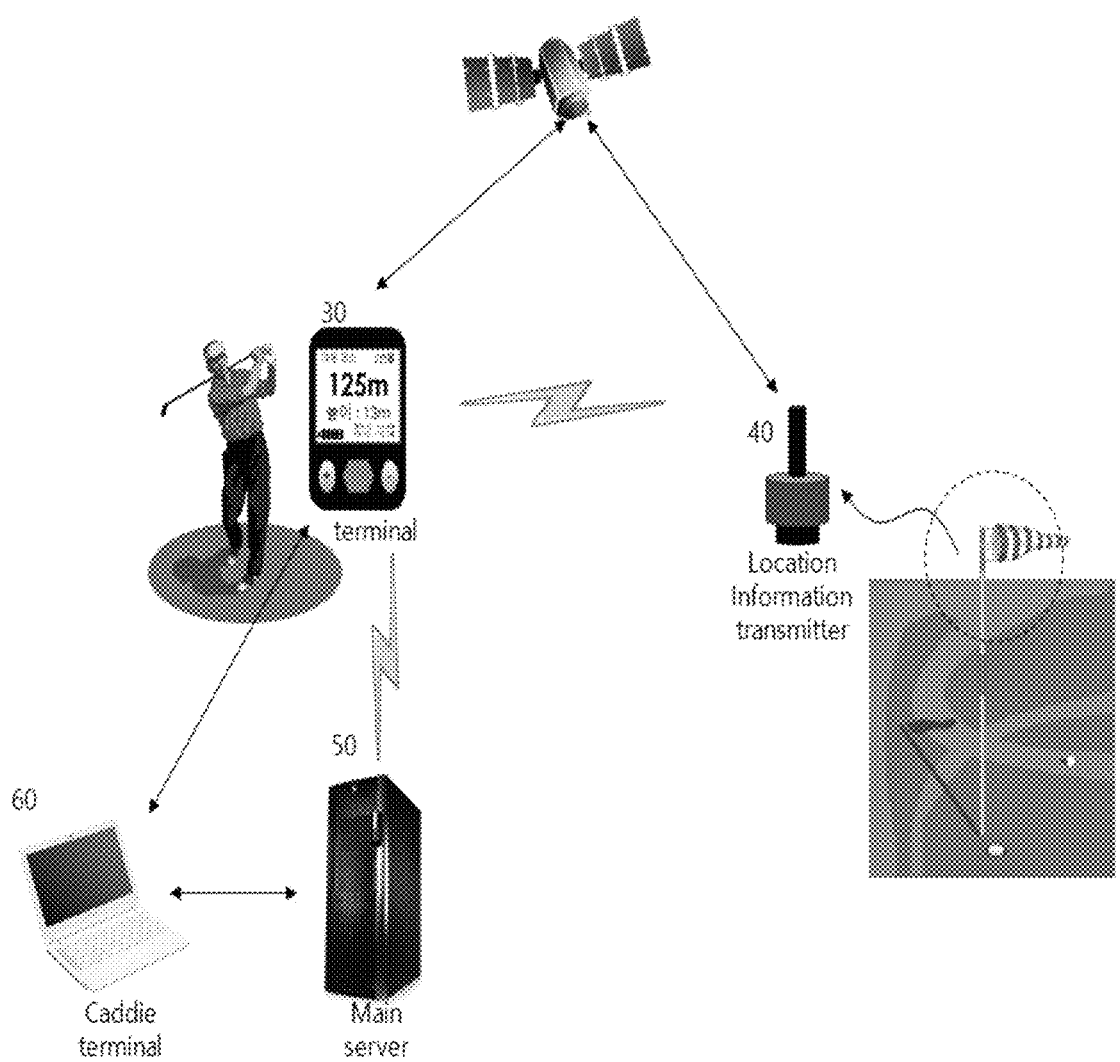

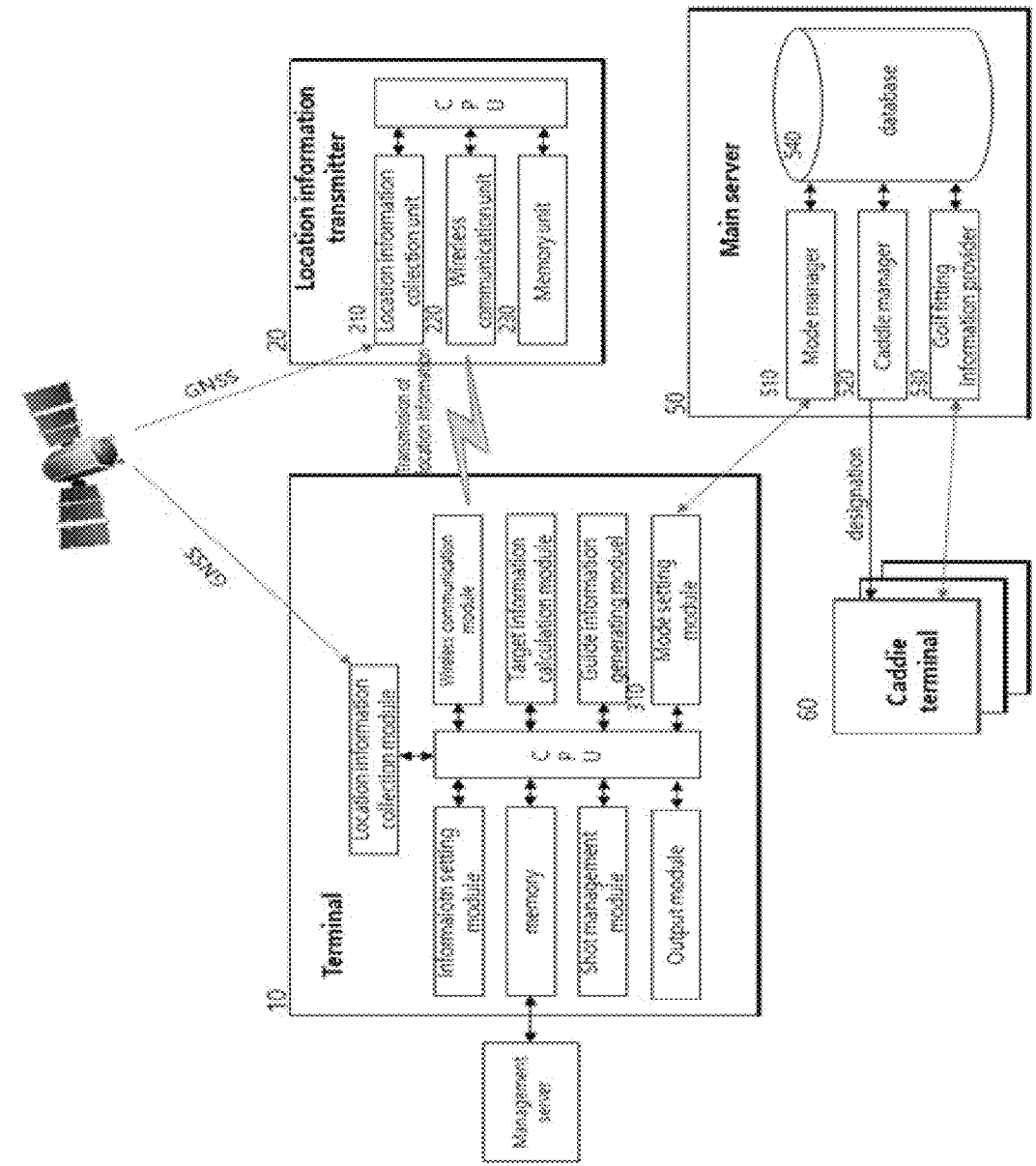
[FIG 8]

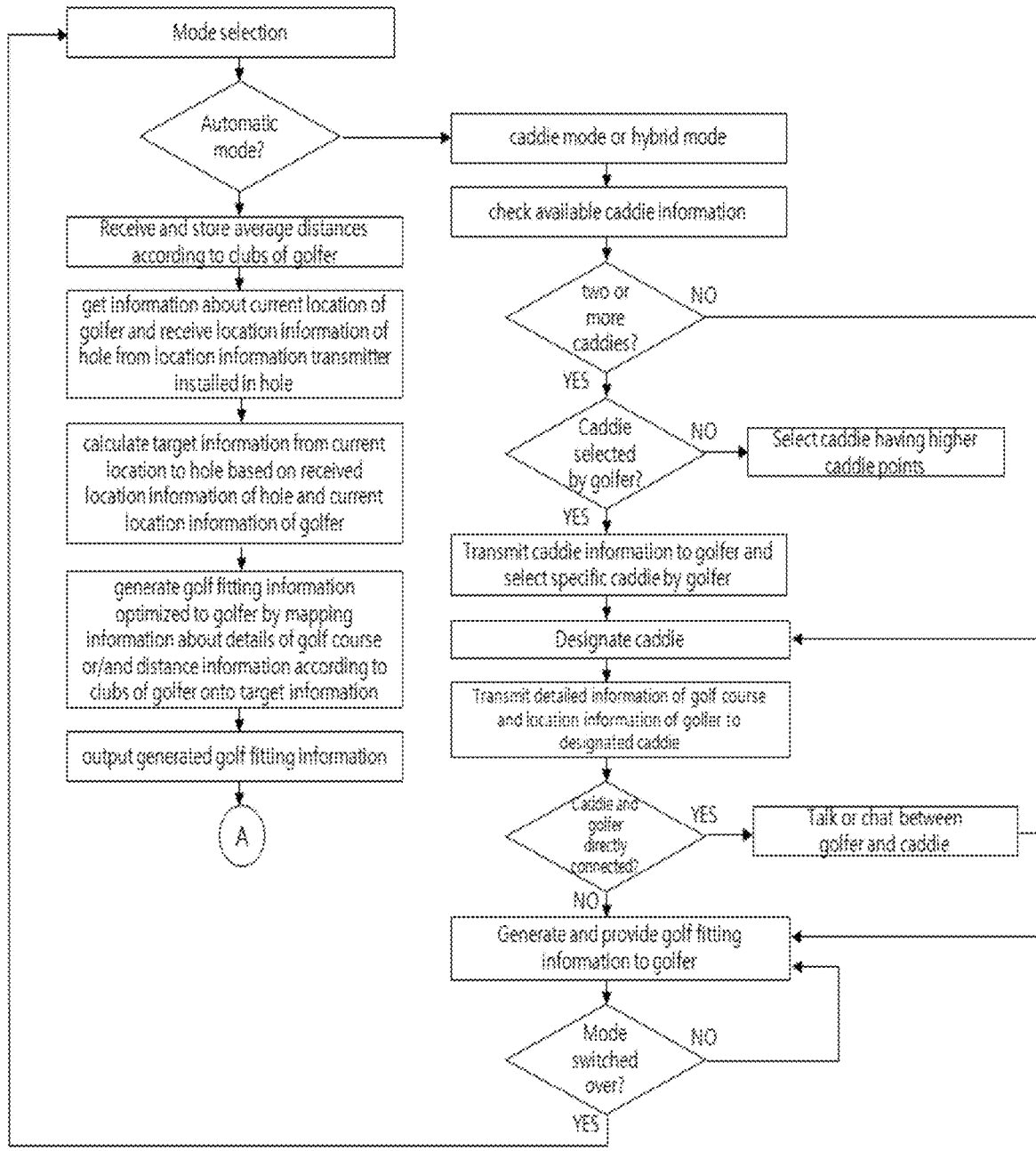
[FIG 9]

[FIG 10]
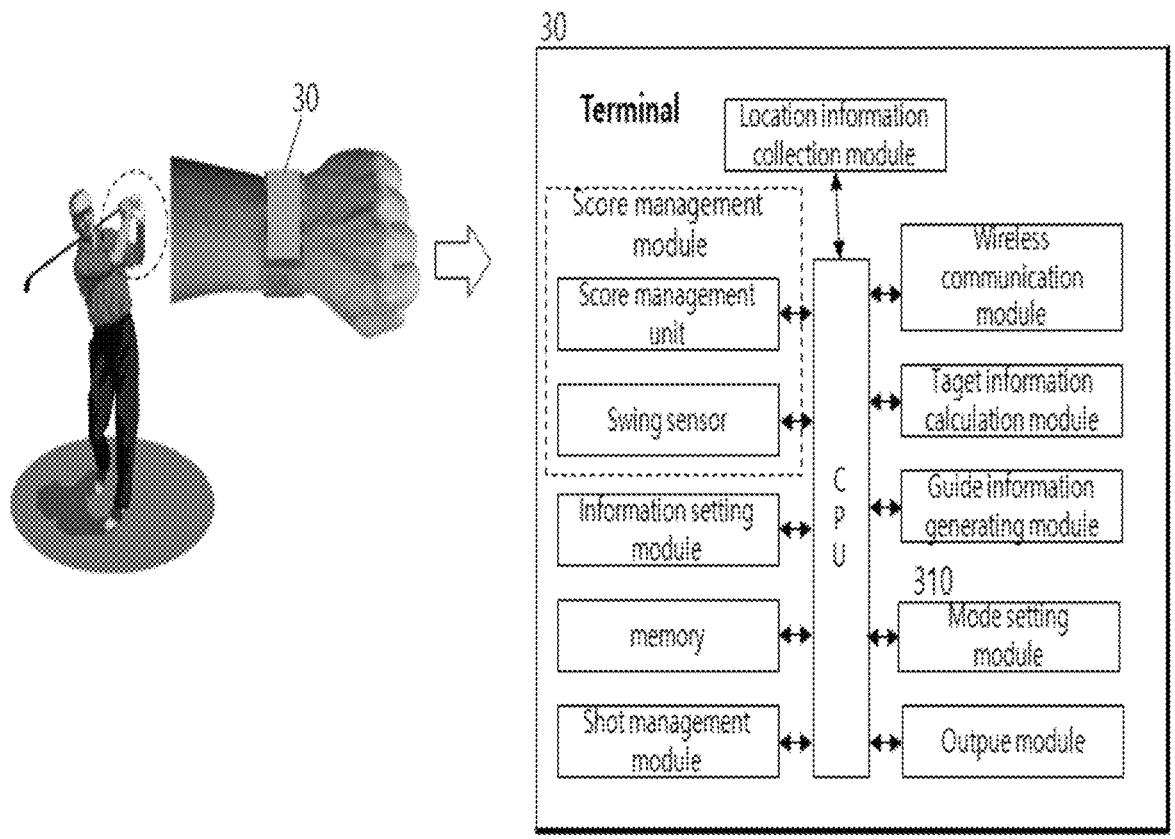

[FIG 11]
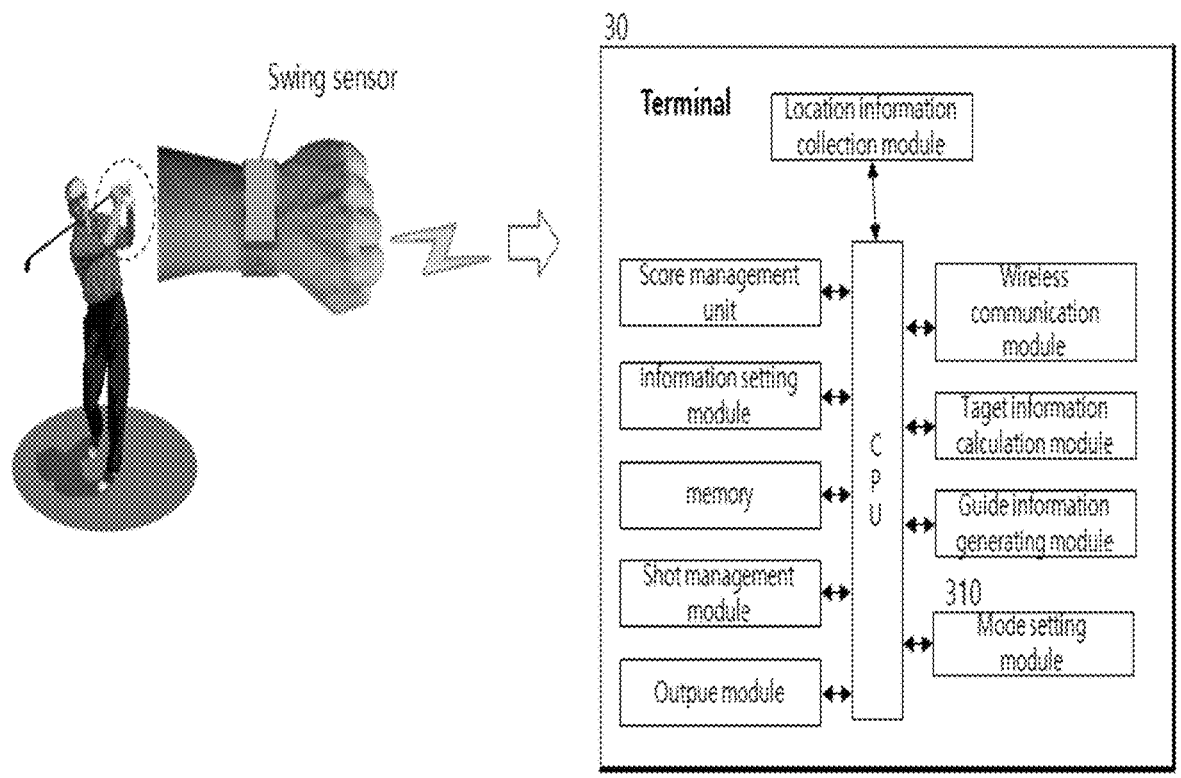

HYBRID GOLF GUIDE SYSTEM

TECHNICAL FIELD

The present invention relates to a golf guide system, and more particularly to a golf guide system in which a user who is playing golf can receive information about a distance and a recommendable club based on analysis of environment and geography between the user's current location and a hole from a faraway caddie through a terminal carried by the user.

BACKGROUND ART

A demand for golf has increased with life enrichment, and the number of golfers using golf courses has also explosively increased year by year due to construction of the golf courses.

In case of playing on the golf course, Par 5 has a distance of 500 m or more, and there are geographical features such as an ascent, a descent, etc. as well as a hazard, a bunker and the like obstacle around a hole. Nevertheless, a shot is made fully depending on information from a caddie.

However, it is likely to miss a shot since the information from the caddie is incorrect, and the caddie merely provides information about a distance or simple cautions but does not provide information about a attack guide customized to skills of a golfer.

To solve such a problem, a rangefinder has been developed to provide a distance from a golfer's current location to a hole on a golf course. However, the rangefinder does not substantially provides the customized information about the attack guide for a hole but provides only simple information about a straight-line distance.

DISCLOSURE

Technical Problem

The present invention is conceived to solve the foregoing problems, and an aspect of the present invention is to provide a golf guide system, which includes a terminal to be carried by a user who is playing golf, and a location information transmitter provided in the terminal and a hole and transmitting location information of the hole to the terminal; generates a distance by measuring a distance between the terminal and the location information transmitter; and generates and provides golf fitting information including a distance and a recommendable club based on analysis of environment and geography between the terminal and the hole in addition to distance information.

Technical Solution

According to an embodiment of the present invention, A hybrid golf guide system includes: a terminal which is carried by a golfer and provides an interface for selecting one mode among an automatic mode for receiving automatically generated golf fitting information, a caddie mode for directly receiving golf fitting information from a faraway caddie, and a hybrid mode; a location information transmitter which is installed in every hole of a golf course and transmits location information of the hole; and a main server which provides golf fitting information in accordance with the modes of the terminal, designates a caddie in the caddie mode, provides information about details of a golfer's ongoing golf course to a caddie terminal of the designated caddie, and transmits the golf fitting information from the caddie terminal to the terminal.

The terminal may include a mode setting module for selecting one mode among the automatic mode, the caddie mode and the hybrid mode, and a score management module which automatically calculates the number of shots or putts of the golfer who carries the terminal and records a score; and the mode setting module may provide an interface for allowing a golfer to select a desired mode in real time, and set the mode in response to an input of the golfer before starting a golf game in a specific golf course, or the mode to be switched over in response to an input of the golfer to receive one-point information or switch over the mode while the golf game is in progress.

The main server may include: a mode manager which sets and manages the automatic mode, the caddie mode and the hybrid mode in response to a request of the terminal; a caddie manager which manages a registered caddie and designates available caddies when there is a need of designating a caddie as the mode is switched over to the caddie mode or the hybrid mode; and a golf fitting information provider which provides information about a location of a golfer who makes a request for the caddie mode and information about the details of the golf courses to the caddie terminal of the designated caddie when the caddie is designated, and transmits the golf fitting information input by the designated caddie to the terminal.

The caddie manager may extract and designate a specific caddie among currently available caddies based on a user database (DB) stored in a database when it is notified of switching over to the caddie mode or the hybrid mode and designating the caddie by the mode manager, and connects the designated caddie to the terminal; and analyze a career about the corresponding golf course, a caddie career, and a carrier about the caddie mode, and designate a caddie who has the highest points as the designated caddie when there are two or more available caddies.

The caddie manager may set a standby mode and manage the available caddies when the available caddies make a request for serving as the caddie through the caddie terminal; and transmit information about available caddies to the terminal in response to a request for the caddie mode or the hybrid mode, and designate a caddie based on a competitive bid in which a golfer selects a specific caddie based on the transmitted caddie information through the terminal.

The golf fitting information provider may provide information about a location of a golfer who makes a request for the caddie mode and information about the details of the golf course to the caddie terminal of the designated caddie, and provide the golf fitting information of the caddie by transmitting the golf fitting information input through the caddie terminal of the designated caddie to the terminal; and provide an interface through which the terminal and the caddie terminal are directly connected by a network so that a golfer and a caddie can talk or chat with each other.

Advantageous Effects

As described above, a golf guide system according to the present invention has outstanding effects on providing not only correct distance information between a golfer's current location and a hole, but also attack guide information optimized by taking details (e.g. an obstacle and geography) of the golf course and skills of the golfer into account, and making it possible to analyze accuracy of shots played by the golfer.

DESCRIPTION OF DRAWINGS

FIG. 1 schematically shows a golf guide system according to a preferred embodiment of the present invention wheelchair according to an embodiment of the present invention, and FIG. 2 is a detailed block diagram of FIG. 1.

FIG. 3 schematically shows that information about details of a golf course is displayed according to an embodiment of the present invention.

FIGS. 4 and 5 are flowcharts of schematically showing a method of providing golf fitting information according to an embodiment of the present invention.

FIG. 6 schematically shows that attack guide information is derived according to an embodiment of the present invention.

FIG. 7 schematically shows a hybrid golf guide system according to the present invention, FIG. 8 is a detailed block diagram of FIG. 7, and FIG. 9 is a flowchart of schematically showing a golf guide method of FIG. 7.

FIGS. 10 and 11 schematically show that a terminal according to the present invention senses a swing motion corresponding to a shot or a putt made by a golfer.

BEST MODE

A golf guide system according to the present invention includes a terminal 10 carried by a user during a golf game and providing golf fitting information based on its own location information and location information received from a location information transmitter; the location information transmitter 20 installed at a hole cup or flag and transmitting the location information of a hole; and a main server managing the terminal and the location information transmitter and transmitting the golf fitting information to the terminal.

Mode for Invention

Below, embodiments of the present invention will be described in detail with reference to the accompanying drawings.

FIG. 1 schematically shows a golf guide system according to a preferred embodiment of the present invention wheelchair according to an embodiment of the present invention, and FIG. 2 is a detailed block diagram of FIG. 1.

Referring to FIGS. 1 and 2, the golf guide system according to the present invention may include a terminal 10 carried by a user during a golf game and providing golf fitting information based on its own location information and location information received from a location information transmitter; the location information transmitter 20 installed at a hole cup or flag and transmitting the location information of a hole; and a main server managing the terminal and the location information transmitter and transmitting the golf fitting information to the terminal.

The terminal 10 may be materialized by an exclusive terminal, but may be achieved in such a manner that an application program is installed in a mobile device such as a smart phone, a tablet PC, etc. Further, the terminal 10 may be manufactured in the form of being attached to a cap, or being wearable on a human body like a watch, a necklace, etc. to be easily carried by a golfer.

The terminal 10 may include an information setting module 110 for setting information related to golf progress; a location information collection module 120 for collecting the location information of the terminal; a target information calculation module 130 for calculating a distance from the location of the terminal to a hole or a target spot based on the location information of the terminal collected in the location information collection module and the location information of the hole received from the location information transmitter; the guide information generation module 140 for generating optimum golf fitting information together with the distance information by analyzing the calculated distance and details of the golf course stored in a memory 150; the memory 150 for storing and managing information about golfers and information about golf courses; a wireless communication module 160 for performing wireless communication with the location information transmitter; and an output module 170 for outputting the generated golf fitting information.

The location information transmitter 20 may include a location information collection unit 210 installed in the hole or flag and collecting the location information; a wireless communication unit 220 wirelessly transmitting the collected location information to the terminal; and a memory unit 230 configured to store unique identification information.

When the location of the hole cup is permanently fixed, the location information of the hole is previously stored. In this case, it is possible to check the location information of the hole. However, in general, the location of the hole is periodically changed on a green, and therefore the location information transmitter is required to determine the location of the hole cup. The location information transmitter is installed in the hole cup or flag, and it is therefore possible to measure the correct location of the hole (pin) even though the location of the hole is changed on the green.

The location information collection module 120 of the terminal and the location information collection unit 210 of the location information transmitter may employ a global navigation satellite system (GNSS) for obtaining the location information through a global positioning system (GPS) or the like satellite.

The target information calculation module 130 of the terminal serves to calculate a straight-line distance between the terminal and the location information transmitter based on the location information collected in the location information collection module 120 of the terminal and the location information received from the location information transmitter 20 installed in the hole.

Since the location information (i.e. GPS information) collected in the terminal 10 and the location information transmitter 20 includes latitude, longitude and altitude information, the target information calculation module 130 can specify the coordinates of the terminal and the coordinates of the hole based on the location information, and calculate the straight-line distance by computing a distance between the coordinates.

The target information calculation module 130 may calculate a correct direction from the terminal to the hole based on the location information (i.e. latitude and longitude) of the terminal and the location information transmitter, and calculate and provide both the straight-line distance and directional information from the current location of the terminal to the hole.

Further, when the location information includes the altitude information, the altitude information received from the hole is compared with the altitude information at the location of the terminal, and it is thus possible to calculate and provide high and low (i.e. slope) information from the location of the terminal to the hole.

The guide information generation module 140 serves to generate the golf fitting information optimized to the current location based on the target information calculated by the target information calculation module 130 and the information about the details of the golf course stored in the memory.

The information about the details of the golf course may be stored in the memory. For example, the information about the details of the golf course previously stored in a database of a management server may be transmitted to the terminal 10 and then stored in the memory.

FIG. 3 schematically shows information about details of a golf course according to an embodiment of the present invention.

Referring to FIG. 3, the information about the details of the golf course may be stored by building a database (DB) of coordinate information, in which the golf course is patterned with a grid at intervals of 1-10 m according to the holes, and the information about the details is set as follows.

Coordinates at tee box locations (e.g. Back, Front, Gold, Lady, etc.) of the holes and range settings (corresponding to a radius of 10 m or a tee box size)

Information about an obstacle (OB) and a hazard at a left limit (LL) and a right limit (RL) in the course Location coordinates and ranges (start coordinates (BS), center coordinates (BC), and end coordinates (BE)) of a bunker Location coordinates and ranges (start coordinates (HS), center coordinates (HC), and end coordinates (HE)) of a hazard Slope information (lie information [slice (CSn), hook (CHn), uphill (ClN), and downhill (CDn)] at the tee box location)

General slope information of a green (uphill/downhill information toward a green, and start coordinates (GS), center coordinates (GC), and end coordinates (GE) of the green)

Thus, the guide information generation module 140 may generate the golf fitting information for the next shot at the current location as shown in FIG. 4 by extracting and mapping the detailed information of the corresponding hole from the calculated target information (i.e. a distance, a direction, high and low) and the golf course information.

As described above, the geography, the slope, etc. of the golf course are accurately generated in units of grid (1-10 m), and therefore a golfer can receive the golf fitting information according to ascending and descending slopes at his/her own location and hit a shot more correctly.

A conventional golf guide system is also capable of providing a shot guide by taking a slope at a current location into account. However, the conventional golf guide system calculates and provides only an overall slope from the current location to the hole, and therefore regards the overall slope as a descent when the overall slope is downhill even though an actual location of a golfer has ascending geography, thereby providing shot information. Like this, it is difficult for the conventional golf guide system to provide correct shot information.

On the other hand, the golf guide system according to the present invention generates information about not only overall geography from a golfer's current location to the hole, but also the geography and slope at the current location of the golfer and directional information, thereby providing shot information in consideration of both the current location and the overall geography when the current location of the golfer has ascending geography even though the overall slope up to the hole is downhill.

In more detail, when the target information calculation module 130 calculates the target information (e.g. distance, direction, high and low) up to the hole from the location of a golfer who carries the terminal 10, the guide information generation module 140 analyzes surrounding environment information between the current location of the golfer and the hole in real time by mapping the target information to sophisticated information about the details of the golf course (e.g. obstacle information (locations of an obstacle, a bunker and a hazard), geography information (e.g. an ascent, a descent, a slice lie and a hook lie), a ground state (e.g. a fairway and a rough), etc.) stored as a database in units of grid (1~10 m), and generates the golf fitting information with the attack guide information related to a detailed hole attack method at the same time when generating and providing cautions for a shot (e.g. a front uphill slope, a right hazard, a bunker 100 m up ahead, etc.) together with the target information.

By the way, as described above, when the information about the details of the golf course is stored in the memory of the terminal, the memory may be overloaded and power consumption may increase. Accordingly, the information about the details of the golf course may be stored in the main server, and the terminal may be configured to search necessary course information from the main server and parse only necessary information.

Here, the attack guide information may be generated by taking a shot skill of an actual golfer into account. To this end, the information setting module 110 of the terminal may receive, store and manage golfer information a (e.g. driving distances according to clubs) input by golfer.

The information setting module 110 serves to set various pieces of golf information, and provide an input interface when a golfer inputs data or selects a menu.

For example, the information setting module 110 may previously receive and set a driver average distance of 200 m, a 7-iron average distance of 120 m, and the like golfer's own average distances according to the clubs, and analyzes the target information and the information about the details of the golf courses based on the settings, thereby generating customized attack guide information.

In general, the attack guide information may be set with respect to the average distances of the clubs. However, the golfers are different in the driving distance from one another in accordance with careers, swing motions and postures, etc., and therefore a large error may occur when the guide information is generated based on the average distances of the general clubs without considering personal skills, thereby making it impossible to provide the customized guide information. On the other hand, according to the present invention, it is possible to provide the attack guide information based on the average distances according to the clubs, directly registered by each individual golfer.

In addition, the golf guide system according to the present invention provides not only the golf fitting information about the shots to a golfer, but also golf history information obtained by analyzing accuracy of a shot when the golfer hits the shot.

To this end, the terminal 10 may further include a shot management module 180.

When a golfer finishes a shot, moves to a location where a ball comes to rest and sets a location of a ball, it is possible to calculate shot information between the previous location and the current location where the ball comes to rest, determine accuracy of the shot based on the shot information, and store and manage the accuracy of the shot as a golfer's history information. The golfer's history information may be used as data for analyzing the golfer's shot accuracy, weakness, etc.

More specifically, when a shot evaluation menu is selected through the information setting module 110, the shot management module 180 stores the location information before the shot, calculates the shot information including moving distance and directional information corresponding to the shot based on the settings about the location information of the ball after the shot, compares the shot information with the golf fitting information provided before the shot, and analyzes and provides the accuracy of the shot.

Further, the shot management module 180 calculates the actual average distances according to the clubs by aggregately managing the shot information, compares the calculated actual average distances with the distance information according to the clubs input and stored by a golfer, and modifies and updates the distance information according to the clubs when the calculated actual average distances is not matched with the stored distance information, thereby generating more accurate golf fitting information.

Since the shot management module 180 is capable of analyzing a shot whenever a golfer hits the shot, it is possible to analyze information about all the shots played by the golfer with regard to all the holes, and aggregately store all the pieces of shot information as the golfer's history information to compensate defects in the shots of the golfer through the analysis of the accuracy of the shot and the golfer's driving distance.

Further, the shot management module 180 may serve as a score board, automatically record scores of a golfer without separately making a score board whenever a golf game is ended, and analyze the golfer's shots with respect to each individual hole.

The wireless communication module of the terminal and the wireless communication unit of the location information transmitter may perform wireless communication based on not only Wi-Fi but also ZigBee, Bluetooth, and the like near field communication. When the location information transmitter transmits the location information, unique identification information of the location information transmitter installed at the hole is transmitted together with the location information, and it is thus possible to identify each hole and selectively receive only the location information from the hole at which the golfer is in progress.

In general, tee shots are all different in location on the golf course, but the hole cups are likely to be closer to each other even at different holes. In this case, two or more pieces of location information are received all together, and therefore only location information of a desired hole is selectively received by identifying the location information of each hole.

Below, a method of providing the golf fitting information according to an exemplary embodiment of the present disclosure will be described.

FIGS. 4 and 5 are flowcharts of schematically showing a method of providing golf fitting information according to an embodiment of the present invention.

Referring to FIGS. 4 and 5, first, information related to golf progress is selected and set through the information setting module.

Here, the information related to the golf progress may include information about a golf course where a golf game is played, and holes, and thus the information about the details of the corresponding golf course is extracted from the memory or downloaded from the management server, and then settings are completed.

For example, in case of a tee shot location of the first hole on an AA golf course, detailed information about the first hole is extracted from information about the details of the AA golf course, and then settings are completed.

Then, when a golfer wants to set his/her own club distance information, the information setting module receives distance information according to the clubs and stores the distance information in the memory.

For example, a golfer may input distance information such as an average driving distance of 180 m, a 9-iron average distance of 100 m, and average distances increasing by 5 m in decrement of the iron number, and may also previously input club information about a club (e.g. wood) that the golfer is poor at, a club (e.g. 7-iron) that the golfer is good at, etc.

The distance information according to the clubs may be used for generating customized guide information when the attack guide information to be provided to a golfer is generated.

When the information is set as described above, a golfer carries the terminal and plays golf.

When the golfer stands at a tee shot location to start the hole, the target information calculation module of the terminal calculates the target information from the current location of the terminal to the location of the hole.

In more detail, the target information calculation module analyzes the location information of the hole (pin) received from the location information transmitter installed in the hole, and the location information about the current location of the terminal through the location information collection module of the terminal, and thus calculates the target information (distance, direction, height difference) from the current location to the hole (pin).

When the target information is calculated as described above, the guide information generation module generates the attack guide information by mapping the golf fitting information the information about the details of the golf courses with regard to the corresponding hole onto the target information.

Here, the golf fitting information may include the target information, the information about the details of the golf courses corresponding to the target information, and the attack guide information at the current location.

When the golf fitting information is generated as described above, the golf fitting information is output through the output module. The output module may output the golf fitting information in an audio form, a video form or combination between audio and video forms through a loudspeaker and a display.

The golf fitting information may give a guide by sequentially outputting the information about the details of the golf courses around the holes, and the attack guide information corresponding to the target information through the output module.

In more detail, when one shot is not enough for an attack the from the current location to the hole (pin) (e.g. when a distance from the current location to the hole is 200 m or longer), the information about the details of the golf courses close to the current location (for example, surrounding geography information, slope information, etc.) is extracted and guided.

For example, information about whether the current location is a fairway or a rough, a distance up to a hazard (when there is the hazard ahead), a distance over the hazard, a distance to a bunker when there is a fairway bunker, and a distance over the bunker is extracted and guided.

Further, information about a slope (e.g. an ascent, a descent, a slice lie, a hook lie, a flatland, etc.) toward a pin is extracted and guided.

For example, in case of the ascent, a club has to be selected by taking a height difference into account, and information may be guided in such a manner that one more club has to be selected in a slope within 10 m, two more club has to be selected in a slope within 10-20 m, and three more club has to be selected in a slope within 20-30 m. In case of the descent, a ball further rolls by a run, and information may be guided in such a manner that one less club has to be selected in a slope within 10 m, two or less clubs have to be selected in a slope within 10-20 m, and three or less clubs have to be selected in a slope within 20-30 m.

In case of the slice lie, information may be guided in such a manner that a play has to be made more leftward than a target direction since a slice is likely to occur as a golf ball is below than feet. In case of the hook lie, information may be guided in such a manner that a play has to be made more rightward than a target direction since a hook or draw is likely to occur as a golf ball is above feet.

On the other hand, when one shot is enough for an attack from the current location to the hole (e.g. the distance shorter than 200 m), pieces of information about distances (GS, GC, CE) to the hole, a slope of a green, obstacles and notices (e.g. a bunker, a hazard, etc.) present in a direction from the current location to the hole (pin), and a slope (e.g. an ascent, a descent, a slice lie, a hook lie, a flatland, etc.) toward the hole is extracted and guided in sequence.

As described above, the attack guide information is generated and guided based on the information about the details of the golf courses around the hole and the distance information according to the clubs set by a golfer.

FIG. 6 schematically shows that attack guide information is derived according to an embodiment of the present invention.

For example, when there is an uphill slope toward the hole, an optimum club may be derived based on a golfer's distance information according to the clubs under a condition that the club has to be selected for a shot distance longer than that of a flatland.

In addition, one more club may be selected in a slope within 10 m, two more club may be selected in a slope within 10-20 m, and three more club may be selected in a slope within 20-30 m.

When a target distance is of 120 m and an uphill slope is of 25 m as shown in FIG. 5, two more club is selected. In this case, for example, when a golfer sets a 7-iron with a distance of 120 m, the attack guide information is generated and guided to use a 5-iron, i.e. a two more club longer than the 7-iron.

When a golfer is located in not a fairway but a rough, the attack guide information may be generated to additionally select a two more club, thereby reflecting information about details of an actual golf course and ability of the golfer.

When another golfer sets a 9-iron with a distance of 120 m, the attack guide information is generated and guided to this golfer to use a 7-iron, thereby providing a guide customized to ability of a golfer.

As described above, the attack guide information may be generated and provided based on the target information between a golfer's current location and the hole location, the information about the details of the golf courses on to which the target information is mapped, and the distance information according to the clubs set by the golfer, thereby providing customized information about a club, a direction and a distance for an accurate shot.

Meanwhile, when a shot is hit based on the golf fitting information, a club used in hitting the shot and a location where a ball comes to rest are designated to thereby generate and provide shot-analysis information for analyzing the accuracy of the shot.

In more detail, when a shot management menu is selected through a setting management module, a club used in hitting a shot is input after hitting the shot based on the golf fitting information, and a location where a ball comes to rest by the shot is set. Then, the shot management module compares the location of the ball before hitting the shot and the location of the ball moved by the shot to thereby calculate a distance and a direction, and compares the club used in hitting the shot and the information to thereby generate shot evaluation information for analyzing the accuracy of the shot.

The information setting module may provide an interface through which a golfer can select a shot analysis menu for getting an evaluation with regard to accuracy, distance, etc. of his/her shot; and store location information before hitting the shot when the shot analysis menu is selected. When the club used in hitting the shot and a ball's current location at a place where the ball moves by the shot and comes to rest, the location information collection module extracts the current location information of the ball.

As described above, when the location information before and after hitting the shot is extracted, a shot analysis module compares the location information before and the location information after hitting the shot to thereby extract the shot information including the moved distance and direction information of the shot, and compares the golf fitting information before hitting the shot and the shot information to thereby analyze the accuracy of the shot.

For example, in the case where the golf fitting information is set with the target distance of 120 m in a flatland, and the golf fitting information is generated to attack with a 7-iron as a golfer's 7-iron has an average distance of 120 m, it may be determined that a slice is caused in a swing when the straight-line distance included in the shot information approximates 120 m but the direction is deflected rightward from the target direction.

Further, when the direction is similar but the driving distance is short, it may be determined that a top ball due to head-up during golf or a duff shot (ground hit) is caused.

The foregoing shot evaluation information is aggregated and managed as a golfer's career information, and the golfer utilizes his/her own shot evaluation information to analyze the accuracy of the shots and the shortcomings of the mis-shots and improve a swing motion or posture.

Further, the shot analysis module is capable of analyzing all the shots from a tee shot to a putt until a ball goes in the hole, and aggregating the number of shots until the ball goes in the hole in response to press of a key after hitting a shot in the hole.

Since the number of shots in each individual hole is recorded through the shot analysis, it is possible to provide score information after a golf game is played with regard to all the holes.

By the way, the method of providing the golf fitting information by the terminal and the method of providing the golf fitting information by the faraway caddie may be hybridized.

That is, a golfer may receive the golf fitting information from the faraway caddie when s/he desires to receive the golf fitting information from the actual caddie while receiving the golf fitting information from the terminal.

FIG. 7 schematically shows a hybrid golf guide system according to the present invention, FIG. 8 is a detailed block diagram of FIG. 7, and FIG. 9 is a flowchart of schematically showing a golf guide method of FIG. 7.

Referring to FIGS. 7 to 9, the hybrid golf guide system according to the present invention may be configured to include a terminal that provides an interface through which an automatic mode for receiving automatically generated golf fitting information or a caddie mode for directly receiving golf fitting information from a faraway caddie is selectable; a location information transmitter that is installed in each individual hole and transmits the location information of the hole; and a main server that provides golf fitting information in accordance with the modes of the terminal, designates a caddie in the caddie mode, provides information about details of a golfer's ongoing golf course to a caddie terminal of the designated caddie and transmits the golf fitting information from the caddie terminal to the terminal.

Here, the terminal and the location information transmitter may be materialized to have the same functions as described in the embodiments of FIGS. 1 to 6.

In more detail, the terminal may further include the mode setting module for selecting one among the automatic mode, the caddie mode and the hybrid mode. Here, the mode setting module provides an interface through which the mode desired by a golfer is selectable in real time.

The mode setting module may set the mode by receiving a golfer's input even before playing golf in a specific golf course, but may set the mode by receiving a golfer's input to receive one-point information or switch the mode while a game is in progress. Further, the hybrid mode may be selected to pursue more detailed shot information.

Here, the hybrid mode provides the golf fitting information from both the automatic mode and the caddie mode at a time, in which a golfer can get more accurate shot information based on comparison in information provided by the two modes.

The main server may be configured to include a mode manager for setting and managing the automatic mode, the caddie mode and the hybrid mode in response to a request of the terminal; a caddie manager for managing a registered caddie and designating an available caddie when the mode is switched over into the caddie mode or the hybrid mode and there is a need of designating the caddie; and a golf fitting information provider for providing information about a location of a golfer who makes a request for the caddie mode and information about the details of the golf course to the caddie terminal of the designated caddie when the caddie is designated, and transmitting the golf fitting information input by the designated caddie to the terminal.

In addition, the main server may further include a database in which information about the registered terminal and the caddie terminal, the information about the details of the golf courses, and the career information are stored and managed.

More specifically, the database (DB) may be configured to include a user DB in which personal information of a registered golfer, the terminal information of the golfer, personal information of a registered caddie, and the terminal information of the caddie are stored and managed; a golf course DB in which information about details of each golf course is stored and managed; a career DB in which plays and records (the number of strokes) of a golfer and a caddie in the specific golf courses, the golf fitting information provided by the caddie, the ranking information of the caddie, etc. are stored and managed.

Here, a golfer's personal information may include a name, identification information, a phone number, age, sex, address, and the like biographical information; and golf experience, an average number of stokes, and the like golf related information. The caddie's personal information may include a name, identification information, a phone number, age, sex, address, and the like biographical information; and a caddie career, a caddie service career according to the present invention, and the like caddie information.

The mode manager serves to receives a request when the mode setting module of the terminal makes the request for switching the mode, and change and manage the ongoing mode into the mode requested by the terminal.

For example, when the terminal makes a request for switching the automatic mode over to the caddie mode, the mode manager makes the terminal enter the caddie mode and requests the caddie manager to designate a caddie.

On the other hand, when there is a request for switching the caddie mode over to the automatic mode, the terminal enters the automatic mode and the caddie manager is notified of termination of providing information to the designated caddie due to mode switching. Meanwhile, when there is a request for switching over from the caddie mode or the automatic mode to the hybrid mode or switching over from the hybrid mode to the caddie mode or the automatic mode, the mode corresponding to the request is operated and subjected to management.

The caddie manager designates the caddie and connects the designated caddie to the terminal when it is notified of switching over to the caddie mode or the hybrid mode and designating the caddie by the mode manager.

In more detail, the caddie manager may extract and designate a specific caddie among currently available caddies based on the caddie DB stored in the database.

Here, when there are two or more available caddies, the caddie manager analyzes the career about the corresponding golf course, the caddie career, and the carrier about the caddie mode, and designates a caddie who has the highest points as the designated caddie.

For example, the caddie whole career, the caddie career in the corresponding golf course, and the caddie mode career are converted into points, and total points are calculated with regard to each individual caddie, thereby selecting the caddie who has the highest total points. Further, the caddie career in the corresponding golf course may be more useful in providing correct shot information than the caddie's own career, and therefore weights may be given to the caddie career in the corresponding golf course when the caddie's points are calculated.

For example, the points may be calculated by (the caddie whole career X 1)+(the caddie career in the corresponding golf course X 1.5)+(the caddie mode career X 1), where, if the career is less than 1 year, it is divided by 12 months so as to be used as a weight (e.g. a career of 6 months is equal to a weight of 0.5, and a career of a year and a half is equal to a weight of 2.5)

Further, when available caddies make a request for serving as the caddie through the caddie terminal, the caddie manager sets a standby mode and manages the available caddies.

When two or more caddies are available, the caddie is designated by not the caddie manager but a golfer's selection.

The caddie manager transmits information about available caddies to the terminal in response to a request for the caddie mode or the hybrid mode, and designates a caddie based on a competitive bid in which a golfer selects a specific caddie based on the transmitted information through the terminal.

Here, the caddie information may be transmitted including the carrier, age, sex and the like information of the caddie. When a paid caddie service is provided, caddie costs (points or prices) proposed by the caddie may be provided together.

Further, a golfer may selects not a single caddie but also a plurality of caddies. In this case, the golfer may receive the golf fitting information from the plurality of caddies and compares pieces of golf fitting information, thereby receiving a correct shout guide.

By the way, a specific caddie may be nominated and designated by a golfer.

For example, a golfer may nominate a desired caddie before or during a golf game. When the desired caddie is available, the caddie manager designates the nominated caddie. Further, the schedules of the caddie may be taken into account to reserve the caddie.

When the caddie is designated as described above, the golf fitting information provider provides information about a location of a golfer who makes a request for the caddie mode and information about the details of the golf courses to the caddie terminal of the designated caddie, and transmits the golf fitting information input through the caddie terminal of the designated caddie to the terminal, thereby providing the golf fitting information of the caddie.

Further, the golf fitting information provider may provide an interface through which the terminal and the caddie terminal are directly connected by a network so that a golfer and a caddie can talk or chat with each other.

In more detail, the golf fitting information provider extracts the information about the details of the golf course, where a golfer is playing golf, from the database through the caddie terminal of the designated caddie, and transmits a golfer's location information from the terminal of the golfer to the caddie terminal.

The designated caddie grasps golf course information from the information about the details of the golf courses, and analyzes information about what number hole the golfer is in, a distance, a geography, a slope and the like details from the current location to the hole, thereby providing shot information to the golfer.

When a golfer's experience information has been stored in the database, the golf fitting information provider transmits the experience information to the designated caddie terminal so that the caddie can provide the shot information in consideration of both the golf course information and a golfer's ability.

The designated caddie provides the golf fitting information at a faraway place, and thus serves as a plurality of caddies for two or more golfers in not a field but a network.

Further, when the caddie business of the designated caddie is terminated, the caddie manager receives and aggregates a satisfaction level or points from the golfer with regard to the caddie, and calculates and provides a caddie ranking to a golfer.

In addition, a golfer may pay for expenses corresponding to a flat rate, a lump sum or the like settlement in case of a paid service, and save points corresponding to the caddie business for the designated caddie, so that the caddie can get money corresponding to the saved points.

Meanwhile, the terminal according to the present invention may further include a score management module that automatically counts the number of shots or putts a golfer hits and records scores.

The score management module may include a swing sensor and a score management unit that determines a shot or putt of a golfer based on a swing motion sensed by the swing sensor and the location information of the golfer, and records a score based on the determination.

In more detail, the swing sensor may include the gyro sensor, and serve to sense the swing motion when a golfer takes a swing for the shot or putt.

According to the present invention, the terminal may be worn on a wrist like a watch as shown in FIG. 10. In this case, the terminal may internally include the swing sensor, or only the swing sensor may be put on the wrist separately from the terminal as shown in FIG. 11.

When the terminal and the swing sensor are separated, the swing sensor may be manufactured to be worn on a wrist like a watch so as to accurately sense the swing motion. In this case, the swing sensor may transmit data to the terminal through near field communication with the terminal. The near field communication may include Bluetooth and the like.

The swing sensor senses the swing motion and transmits it to the terminal. The score management unit receives a golfer's location information from the location information collection module 120 and determines whether a golfer actually hits a shot or putt based on a swing motion signal and a golfer's location information.

For example, when a plurality of successive swing motion signals is sensed and there are no changes in a golfer's location, it is determined as test swings. On the other hand, when a golfer moves after a plurality of swing motion signals, the last swing motion signal is determined as a swing corresponding to an actual shot and then scored.

In general, a golfer takes the test swings before hitting the shot or putt, and it is thus difficult to correctly sense the actual shot or putt. However, the score management module according to the present invention receives a golfer's location information from the location information collection module 120 when receiving a swing motion signal from the swing sensor, and determines the last swing motion in the same location as the shot or putt, thereby recording scores.

For example, when a golfer takes three test swings and then hits the shot, the swing sensor senses four swings of the golfer and transmits four swing motion signals to the terminal. The score management module determines whether the golfer moves or not during four swing motions. When it is sensed that the golfer moves after four swing motion signals, the score management module may determine the fourth swing of the golfer as the actual shot.

Therefore, the test swing and the actual shot are distinguishable among the swing motions, thereby recording only the actual shots.

Further, when a golfer's location information moves from a specific hole to a new hole, the score management unit records the number of previously recorded strokes as scores of a previous hole, and is reset at a start hole to record and manage the number of strokes.

In more detail, the score management unit starts counting the number of strokes when a golfer is in a start location of a specific hole based on the location information of the golfer, senses and counts the actual shots or putts based on a swing motion signal and a location signal, records and resets the number of strokes counted in this hole when it is determined based on the location information that a golfer is in a start location of the next hole, and then records the number of strokes in the next hole. Through the foregoing processes, the number of strokes is recorded with regard to all the holes, and aggregated to record a golfer's scores when a game is over.

Although a few exemplary embodiments of the present invention have been shown and described, it will be appreciated by those skilled in the art that changes may be made in these embodiments without departing from the principles and spirit of the invention, the scope of which is defined in the appended claims and their equivalents.

INDUSTRIAL APPLICABILITY

The present invention relates to a golf guide system, and more particularly a golf guide system in which a user who is playing golf can receive information about a distance and a recommendable club based on analysis of environment and geography between the user's current location and a hole from a faraway caddie through a terminal carried by the user, and which is very useful for industry of golf as leisure sports since the user can easily play and manage a golf game without a caddie.

The invention claimed is:

1. A hybrid golf guide system comprising:
   a terminal which is carried by a golfer and provides an interface for selecting one mode among an automatic mode for receiving automatically generated golf fitting information, a caddie mode for directly receiving golf fitting information from a faraway caddie, and a hybrid mode;
   a location information transmitter which is installed in every hole of a golf course and transmits location information of the hole; and
   a main server which provides golf fitting information in accordance with the modes of the terminal, designates a caddie in the caddie mode, provides information about details of a golfer's ongoing golf course to a caddie terminal of the designated caddie, and transmits the golf fitting information from the caddie terminal to the terminal,
   wherein the terminal comprises a mode setting module for selecting one mode among the automatic mode, the caddie mode and the hybrid mode, and a score management module which automatically calculates the number of shots or putts of the golfer who carries the terminal and records a score,
   wherein the mode setting module provides an interface for allowing a golfer to select a desired mode in real time, and sets the mode in response to an input of the golfer before starting a golf game in a specific golf course, or the mode to be switched over in response to an input of the golfer to receive one-point information or switch over the mode while the golf game is in progress,
   wherein the score management module comprises a swing sensor for sensing a swing motion corresponding to a golfer's shot or putt, and a score management unit for determining the golfer's shot or putt based on the swing motion sensed by the swing sensor and location information of the golfer and records a score based on the determined shot or putt,
   wherein the main server comprises: a mode manager which sets and manages the automatic mode, the caddie mode and the hybrid mode in response to a request of the terminal; a caddie manager which manages a registered caddie and designates available caddies when there is a need of designating a caddie as the mode is switched over to the caddie mode or the hybrid mode; and a golf fitting information provider which provides information about a location of a golfer who makes a request for the caddie mode and information about the details of the golf courses to the caddie terminal of the designated caddie when the caddie is designated, and transmits the golf fitting information input by the designated caddie to the terminal.

2. The hybrid golf guide system according to claim 1, wherein:
   the swing sensor is manufactured to be worn on a wrist like a watch to accurately sense a swing motion and transmit data to the terminal through near field communication with the terminal, and
   the score management unit receives location information of a golfer from a location information collection module when the swing sensor senses a swing motion, and determines whether a golfer actually hits a shot or putt based on a swing motion signal and the location information of the golfer.

3. The hybrid golf guide system according to claim 2, wherein the score management module
   determines a swing motion signal as a test swing when a plurality of successive swing motion signals is sensed and there are no changes in a golfer's location, and determines a last swing motion signal as a swing corresponding to an actual shot and records a score when a golfer moves after a plurality of swing motion signals; and
   starts counting the number of strokes when a golfer is in a start location of a specific hole based on the location information of the golfer, senses and counts the actual shots or putts based on a swing motion signal and a location signal, records and resets the number of strokes counted in this hole when it is determined based on the location information that the golfer is in a start location of the next hole, and records the number of strokes in the next hole, through the foregoing processes, the number of strokes is recorded with regard to all the holes, and aggregated to record a golfer's scores when the golf game is over.

4. The hybrid golf guide system according to claim 1, wherein the caddie manager
   extracts and designates a specific caddie among currently available caddies based on a user database (DB) stored in a database when it is notified of switching over to the caddie mode or the hybrid mode and designating the caddie by the mode manager, and connects the designated caddie to the terminal; and
   analyzes a career about the corresponding golf course, a caddie career, and a carrier about the caddie mode, and designates a caddie who has the highest points as the designated caddie when there are two or more available caddies.

5. The hybrid golf guide system according to claim 4, wherein the caddie manager
   sets a standby mode and manages the available caddies when the available caddies make a request for serving as the caddie through the caddie terminal; and
   transmits information about available caddies to the terminal in response to a request for the caddie mode or the hybrid mode, and designates a caddie based on a competitive bid in which a golfer selects a specific caddie based on the transmitted caddie information through the terminal.

6. The hybrid golf guide system according to claim 1, wherein the golf fitting information provider
   provides information about a location of a golfer who makes a request for the caddie mode and information about the details of the golf course to the caddie terminal of the designated caddie, and provides the golf fitting information of the caddie by transmitting the golf fitting information input through the caddie terminal of the designated caddie to the terminal; and provides an interface through which the terminal and the caddie terminal are directly connected by a network so that a golfer and a caddie can talk or chat with each other.

\* \* \* \* \*